United States Patent
Chen et al.

(10) Patent No.: US 9,445,996 B2
(45) Date of Patent: *Sep. 20, 2016

(54) EXTENDED PRODUCTION OF NITRIC OXIDE FROM A MICROENCAPSULATED NITRITE SALT AND AN AQUEOUS ACIDIFIED GEL

(71) Applicant: NIOXX LLC, Dickinson, TX (US)

(72) Inventors: Cheng-Shing Chen, Taichung (TW); Ferid Murad, McLean, VA (US); Kenneth A Smith, Houston, TX (US); William A Seitz, Dickinson, TX (US); William J Merrell, Galveston, TX (US); Alexandru T Balaban, Galveston, TX (US)

(73) Assignee: NIOXX LLC, Dickinson, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/969,262

(22) Filed: Aug. 16, 2013

(65) Prior Publication Data

US 2014/0056963 A1    Feb. 27, 2014

Related U.S. Application Data

(60) Provisional application No. 61/692,328, filed on Aug. 23, 2012, provisional application No. 61/707,276, filed on Sep. 28, 2012.

(51) Int. Cl.
| | |
|---|---|
| *A61K 9/14* | (2006.01) |
| *A01N 59/14* | (2006.01) |
| *A61K 9/70* | (2006.01) |
| *A61K 33/00* | (2006.01) |
| *A61K 31/341* | (2006.01) |

(Continued)

(52) U.S. Cl.
CPC ............... *A61K 9/14* (2013.01); *A01N 59/14* (2013.01); *A61K 9/06* (2013.01); *A61K 9/5047* (2013.01); *A61K 9/5052* (2013.01); *A61K 9/70* (2013.01); *A61K 31/19* (2013.01); *A61K 31/194* (2013.01); *A61K 31/341* (2013.01); *A61K 31/375* (2013.01); *A61K 33/00* (2013.01); *A61K 33/22* (2013.01); *A61K 47/36* (2013.01); *A61K 45/06* (2013.01)

(58) Field of Classification Search
None
See application file for complete search history.

(56) References Cited

U.S. PATENT DOCUMENTS 4,332,790 A * 6/1982 Sozzi et al. .................. 424/498
5,804,213 A    9/1998 Rolf (Continued)

FOREIGN PATENT DOCUMENTS

GB    WO99/44622 A1    9/1999

OTHER PUBLICATIONS

Butler, Anthony R. et al., "Therapeutic Uses of Inorganic Nitrite and Nitrate: From the Past to the Future," Circulation vol. 117 (2008) 2151-2159.

(Continued)

Primary Examiner — Isaac Shomer
(74) Attorney, Agent, or Firm — Blank Rome LLP

(57) ABSTRACT

Methods and compositions are provided for generating and applying long-lasting therapeutic nitric oxide (NO) gas from the reaction of a least one microencapsulated nitrite salt and an activating volume of an aqueous acidified gel that has sufficient acidity to convert the nitrite salt to a nitric oxide (NO) and further provides a reducing property that retains the NO in bioactive form.

16 Claims, 6 Drawing Sheets

(51) Int. Cl.
*A61K 33/22* (2006.01)
*A61K 31/194* (2006.01)
*A61K 47/36* (2006.01)
*A61K 9/06* (2006.01)
*A61K 9/50* (2006.01)
*A61K 31/19* (2006.01)
*A61K 31/375* (2006.01)
*A61K 45/06* (2006.01)

(56) References Cited

U.S. PATENT DOCUMENTS

| | | | |
|---|---|---|---|
| 5,910,316 A * | 6/1999 | Keefer et al. | 424/433 |
| 5,994,444 A | 11/1999 | Trescony | |
| 6,103,275 A * | 8/2000 | Seitz et al. | 424/718 |
| 7,048,951 B1 * | 5/2006 | Seitz | A61K 9/0014 |
| | | | 424/718 |
| 7,968,575 B2 | 6/2011 | Assaf | |
| 8,980,331 B2 * | 3/2015 | Chen | A61K 9/14 |
| | | | 424/718 |
| 2002/0119115 A1 | 8/2002 | Keefer | |
| 2003/0026849 A1 | 2/2003 | Thomas | |
| 2003/0064028 A1 | 4/2003 | Fine et al. | |
| 2006/0182815 A1 * | 8/2006 | Gladwin et al. | 424/718 |
| 2006/0198796 A1 | 9/2006 | Giniger | |
| 2007/0089739 A1 * | 4/2007 | Fine et al. | 128/202.26 |
| 2008/0184618 A1 | 8/2008 | Darlington | |
| 2009/0136410 A1 | 5/2009 | Smith | |
| 2009/0216204 A1 | 8/2009 | Bhavaraju | |
| 2009/0220450 A1 | 9/2009 | Green | |
| 2009/0297634 A1 * | 12/2009 | Friedman et al. | 424/718 |
| 2009/0311292 A1 | 12/2009 | Pacheco | |
| 2010/0129474 A1 | 5/2010 | Benjamin | |
| 2011/0250134 A1 | 10/2011 | Cabrales | |
| 2012/0136323 A1 | 5/2012 | Stasko | |
| 2013/0330244 A1 * | 12/2013 | Balaban | A61K 33/00 |
| | | | 422/225 |

OTHER PUBLICATIONS

Cabrales, Pedro et al., "Sustained Release Nitric Oxide from Long Lived Circulating Nanoparlicles," Free Radic Biol Med vol. 49(4) (2010) 530-538.

Englander, Laura, MD et al., "Nitric Oxide Nanoparticle Technology—A Novel Antimicrobial Agent in the Context of Current Treatment of Skin and Soft Tissue Infection," The Journal of Clinical and Aesthetic Dermatology, vol. 3, No. 6 (2010) 45-50.

International Search Report and Written Opinion regarding corresponding PCT Application No. PCT/US2013/055428, dated Apr. 7, 2014.

* cited by examiner

EXTENDED PRODUCTION OF NITRIC OXIDE FROM A MICROENCAPSULATED NITRITE SALT AND AN AQUEOUS ACIDIFIED GEL

CROSS REFERENCE TO RELATED APPLICATIONS

This application claims priority based on U.S. Provisional Application Ser. No. 61/692,328 filed Aug. 23, 2012, and 61/707,276 filed Sep. 28, 2012, which are incorporated herein by reference.

FIELD OF THE INVENTION

This invention relates to compositions and methods for generating and applying nitric oxide locally.

BACKGROUND OF THE INVENTION

Without limiting the scope of the invention, its background is described in connection with application of nitric oxide in medical indications and with compositions and methods for extended nitric oxide (NO) generation and application locally.

The biological importance of NO is well documented. See e.g. Lancaster J R. *Proc Natl Acad Sci* 91 (1996) 8137-41; Ignarro et al. *Proc Natl Acad Sci* 84 (1987) 9265-69; reviewed in Bredt D S, *J Cell Science* 116 (2003) 9-15; reviewed in Murad F, *N Engl J Med* 355 (2006) 2003-11. In mammals, NO is an endogenous physiological mediator of many processes in the nervous, immune and cardiovascular systems. These include vascular smooth muscle relaxation, which results in arterial vasodilation and increased blood flow. NO is also a neurotransmitter and has been associated with neuronal activity and various functions ranging from avoidance learning to genital erection in males and females (Kim et al., *J. Nutrition* 134 (2004) 28735). NO also partially mediates macrophage cytotoxicity against microbes and tumor cells. Besides mediating normal functions, NO is implicated in pathophysiologic states as diverse as septic shock, hypertension, stroke, and neurodegenerative diseases.

NO has been applied pharmacologically in various forms. See Butler and Feelisch, *Circulation* 117 (2008) 2151-59. One must note, however, that NO itself is highly reactive and is not chemically stable in air or in the body. Therefore, its pharmacological applications almost invariably involve its production via a chemical reaction of various individually-stable precursor compounds. Organic and inorganic nitrates acting as NO donors such as nitroglycerin and sodium nitroprusside have long been used to correct NO deficient states or to regulate the activities of many tissues. Topical applications of NO may be used to help wound and burn healing, hair growth, impotence, and to cause vasodilatation where needed (e.g., promoting peripheral blood flow in patients with impaired circulation due to diabetes or other conditions and ripening of the cervix in pregnancy). Local high concentrations of NO (eye, skin, e.g.) are tolerated. Smith et al. (U.S. Pat. No. 5,519,020) describes polymeric nitric oxide sources thought to be useful to promote healing.

In a range of topical applications, a low persistent dose of NO is desired. NO serves as a powerful microbicide that is effective against antibiotic-resistant bacteria. In anti-microbial and other topical applications, the NO needs to be maintained in contact with the skin for an extended period of time. In anti-microbial applications, the therapeutically-effective NO dose can be small, only a few hundred parts per million (ppm) (see, for example, Ghaffari et al., *Nitric Oxide Biology and Chemistry* 14 (2009) 21-29), but the effectiveness of the NO depends substantially on how long the skin contact is maintained (Omerod et al., *BMC Research Notes* 4 (2011) 458-465).

A technology for topical release of NO is described in Seitz et al U.S. Pat. No. 6,103,275 and the co-pending application of Seitz et al (U.S. Ser. No. 13/688,511, filed Nov. 29, 2012), which are incorporated herein by reference. However, this technology provides a topical NO dose that lasts for less than one hour, and an alternate approach is needed to provide the lengthy NO skin contact required for many therapeutic applications.

SUMMARY OF THE INVENTION

Provided herein are compositions, methods and medical devices for local pharmaceutical application of therapeutically-effective amounts of NO via a reaction of reagents, some or all of which are initially provided in microencapsulated form.

In one embodiment, a microencapsulated reagent is provided to react in a gelatinous composition that contains a solution of one reagent that reacts with the microencapsulated reagent as it is slowly released from its microcapsules. This embodiment provides a time-released dose of NO over extended periods of time.

In another embodiment, two or more microencapsulated water-soluble reagents are provided that react to form a therapeutic NO agent that is time-released over extended periods of time.

One aspect of the present disclosure is a method in which the microparticles containing water-soluble reagents are subjected to an amount of water necessary only to moisten the surfaces of the particles. This method is particularly useful because it substantially prolongs the release time of the reagents beyond the release time that would be observed if only one type of microcapsule were immersed in an excess of water. This, in turn, prolongs the time during which the therapeutic agent is available, compared to that of a time-release composition based upon the direct release of a single therapeutic agent from a microencapsulation vehicle.

In one embodiment, a method is disclosed for generating extended release therapeutic nitric oxide including providing a mixture of two or more types of sub-millimeter-scale microparticles, where each type of particle contains only one kind of microencapsulated reactant. The mixture comprises at least one microencapsulated nitrite salt, at least one microencapsulated acid, and at least one microencapsulated reducing agent and further providing an activating volume of water sufficient to incipiently wet the microencapsulated reactant particles, wherein the activating volume of water is added to the microencapsulated reactants and extended release production of NO is initiated via a nitrous acid intermediate. In one embodiment ascorbic acid serves as both the acid and the reductant.

The mixture of sub-millimeter-scale microencapsulated reactants is provided in a wound dressing or bandage in certain embodiments. The sub-millimeter-scale microencapsulated reactants may be provided in a moisture-proof unit dose container that is sealed until use. When needed, the container is opened and the reactants administered to a tissue site in need of treatment. The container may be a wound dressing or bandage or may be a container of dry powder reactants that are poured or sprinkled on the tissue. In one embodiment, an activating volume of sterile water is provided together with the unit dose of reactants with instructions for administration. In certain embodiments, a plurality of premeasured amounts of water are provided including an activating volume and one or more reactivating volumes with instructions to add reactivating volumes at intervals after the initial activation. The reactants and activating/reactivating water or an aqueous gel together with instructions is provided in kit form in certain embodiments.

The present NO generation method through microencapsulation of chemical reactants is useful because it provides for the prolonged production of an unstable compound (such as NO) from precursors that are in a chemically-stable form. Multiple microencapsulated reactants can readily be stored mixed and in contact with one another in a dry environment, and the production of NO can be initiated simply by providing a small amount of water to the precursor mixture. Alternatively, such a mixture of microencapsulated reactants can be applied directly to a wound, wherein the wound environment itself provides sufficient water to cause release of therapeutic amounts of NO. A further advantage is that the volume occupied by the reagents and water is relatively small, promoting incorporation of this invention into dimensionally-limited objects. Such objects would include wound dressings, bandages, and other physically-thin medical articles and also physically-small medical articles such as vascular and other stents, catheters, pacemakers, defibrillators, heart assist devices, artificial valves, electrodes, orthopedic screws and pins and other medical articles routinely implanted or inserted into the body.

In an alternative embodiment, microencapsulated nitrite is mixed with activating reactants that are in gel form. The gel slows the interaction between the nitrite and the activating reagents resulting in higher levels of dissolved NO as well as prolonged NO release. The materials and methods disclosed in this embodiment result in an increase the amount of NO produced over a several-hour period, compared to the amount that would be observed when two or more types of particles individually containing appropriate reagents are immersed together in an excess of water or water-based liquids.

DETAILED DESCRIPTION

Figure 1:
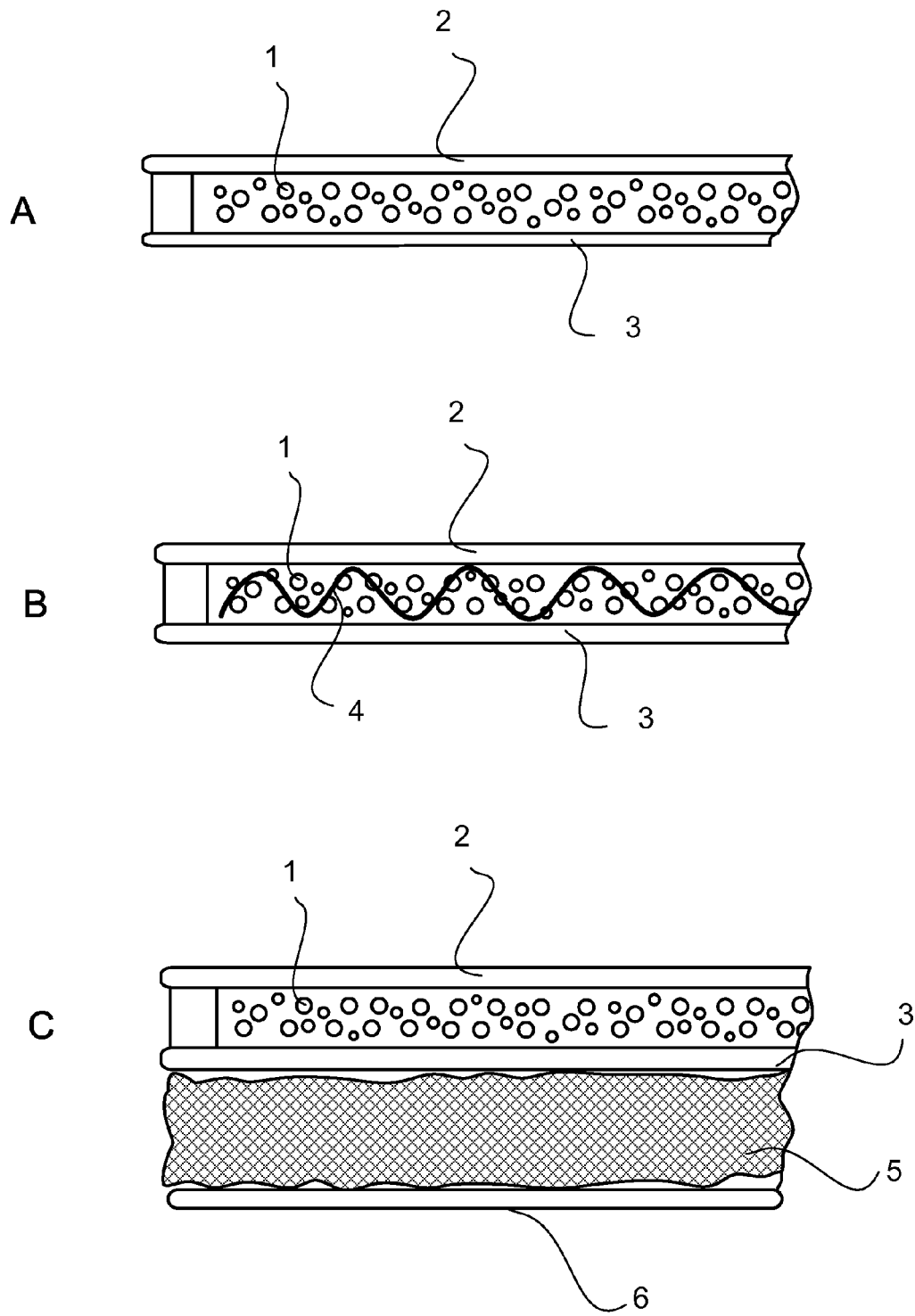
FIG. 1A is a cross-sectional view of an embodiment of a pad containing a mixture of microencapsulated reagents that react to produce NO.
FIG. 1B shows a cross-sectional view of a pad incorporating an internal element to keep the microparticles in place.
FIG. 1C is a cross-sectional view of an embodiment of an absorbent bed-pad incorporating microencapsulated reagents that react to produce NO.

Provided herein are methods, apparatus and compositions that deliver long-lasting dosage of NO in topical applications by microencapsulating NO producing reactants. In one embodiment the microencapsulation vehicle is a polymer matrix. The reagents and matrix together are incorporated in sub-millimeter-scale structures that have at least one dimension less than a millimeter. Such structures can be particles, fibers or films.

One pharmaceutically-acceptable way of producing NO employed herein relies on the chemistry of nitrous acid ($HNO_2$). Nitrous acid is produced from inorganic nitrites on treatment with acids (HA) according to equation (1) below. Nitrous acid is stable in aqueous solution at low temperature, but it decomposes into NO and $NO_2$ readily at room temperature according to the equation (2).

In the presence of a reducing agent (such as ascorbic acid, $Asc(OH)_2$), the $NO_2$ is readily converted to NO as shown in equation (3) below.

$$2HA + 2NaNO_2 \rightarrow 2HNO_2 + 2NaA \tag{1}$$

where HA is an organic acid $$2HNO_2 \rightarrow NO + NO_2 + H_2O \tag{2}$$

nitrous acid decomposes generating nitrogen dioxide $$NO + NO_2 + H_2O + Asc(OH)_2 \rightarrow 2NO + 2H_2O + AscO_2 \tag{3}$$

the ascorbic acid reacts to remove the nitrogen dioxide

In one embodiment of this invention, a microencapsulated reagent is mixed with a composition that provides an appropriate environment for release and reaction of that reagent to produce NO over an extended period of time. When the microencapsulated materials come into contact with water (or an aqueous solution), the liquid slowly penetrates the particles and NO-producing reactants are liberated slowly over time. The reactants then take part in reactions that produce NO.

One such embodiment of the invention utilizes a microencapsulated nitrite salt and an aqueous acidified gel with sufficient acidity to convert the nitrite salt to nitric oxide. A reductant to help retain the nitric oxide in bioactive form is preferably included in the gel. The acidifying agent is preferably an organic acid such as citric acid, although inorganic acids such as boric acid, for example may also be suitable. Other acidifying agents may include lactic acid, glyceric acid, formic acid or other organic acids known to those of skill in the art. Inorganic acids with the appropriate pKa values can also be used if they are biologically acceptable (e.g. the aforementioned boric acid). The gel acidifying agent may also be a reductant, such as ascorbic acid (vitamin C) or an ascorbic acid derivative including but not limited to, 3-O-ethyl ascorbic acid, other 3-alkyl ascorbic acids, 6-O-octanoyl-ascorbic acid, 6-O-dodecanoyl-ascorbic acid, 6-O-tetradecanoyl-ascorbic acid, 6-O-octadecanoyl-ascorbic acid, and 6-O-dodecanedioyl-ascorbic acid. The preferred reductant is one having the reductive capability of preventing or slowing the oxidation of nitric oxide to nitrogen dioxide and also having the capability of directly reducing $NO_2$ to NO so that the gas released by the composition is predominantly NO. Preferred reductants include ascorbic acid, ascorbic acid derivatives, ascorbate salts, tocopherol, erythrobates or alpha-tocopherol. Gelling agents include substances such as hydroxymethyl cellulose, hydroxyethyl cellulose, gelatin, agar, natural gums, starches and pectins.

The medium for dissolution of the acid and reductant may be an aqueous medium or a nonaqueous medium. Aqueous media are generally preferred and readily prepared as gels. The acidic gel composition may additionally contain the conjugate base of one or more of the acids used. While the base is preferably the conjugate base of the acid used, but can be another organic or inorganic base known to those of skill in the art. This embodiment of the invention may be applied directly to the skin stimulate circulation, to wounds to speed their healing, to the scalp and maintained there for a period of time as a treatment to stimulate hair growth, and it may be applied in any other application where local release of NO is beneficial.

Another embodiment of this invention is a kit for delivering an acidified gel and a microencapsulated nitrite salt. The acidified gel and the microencapsulated nitrite salt are individually packaged in moisture-proof packages, which are opened and their contents mixed together immediately prior to application of the mixture. In an alternative embodiment, the microencapsulated nitrite salt and the acidifying agents are packaged either together or individually in moisture-proof packages. The packages are opened and their contents are mixed with a measured amount of water or a pH-neutral aqueous gel prior to application of the mixture.

Another embodiment utilizes a mixture of two or more types of microparticles, where each type of particle comprises only one kind of microencapsulated reagent. The particles in the mixture collectively contain reagents that react with one another to produce NO. For instance, one type of particle in the mixture could contain sodium nitrite and another type could contain ascorbic acid, which when released together in solution will react to produce NO. The particles in which the reagents are microencapsulated are maintained in close physical proximity to one another in a limited volume, and a limited amount of water residing within that same volume is used to extract and process the reagents to produce the therapeutic agent.

By limited amount of water it is meant sufficient water to incipiently wet the dry microencapsulated reactant particles thereby permitting the reactants to interact and chemically react. Incipient wetness means a volume of the liquid sufficient to wet the reactant particles without excess liquid present after addition of the liquid to the dry reactant particles.

One embodiment of the present invention utilizes a microencapsulated nitrite salt, a microencapsulated acid, and a microencapsulated reducing agent. Various nitrite salts may be used, most commonly inorganic ones, such as sodium nitrite, although potassium nitrite, calcium nitrite, or any alkali metal nitrite or alkaline earth nitrite are usable. For certain indications, the reducing agent is selected to have the reductive capability of preventing or slowing the oxidation of nitric oxide (NO) to nitrogen dioxide ($NO_2$), and also having the capability of directly reducing $NO_2$ to NO so that the gas released by the composition is predominantly NO. Suitable reductants include ascorbic acid, ascorbate salts, tocopherols (including particularly alpha tocopherol), erythrobates, carotenoids, tocotrienols and thiols.

Citric acid is one acceptable organic acid. Other acids may include lactic acid, glyceric acid, formic acid or other organic acids known to those of skill in the art. Inorganic acids with the appropriate pKa values can also be used if they are biologically acceptable (e.g. boric acid). In an embodiment providing ascorbic acid as the acid, the ascorbic acid serves both as the organic acid and the reducing agent. Ascorbic acid (vitamin C) is one biocompatible reducing agent for nitrites.

One production method for microencapsulation is spray-drying of a melt or polymer solution of one of the reagents to produce a finely-divided powder of individual particles comprising that reagent dispersed within a polymer matrix. Other microencapsulation methods such as pan coating, air suspension coating, centrifugal extrusion, fiber spinning, fiber extrusion, nozzle vibration, ionotropic gelation, coacervation phase separation, interfacial cross-linking, in-situ polymerization and matrix polymerization may also be used.

For purposes of the medical indications disclosed herein, the encapsulation polymer is a biocompatible polymer. Suitable polymers include ethyl cellulose, natural polymers such as zein (a prolamine seed storage protein found in certain grass species including maize and corn), chitosan, hyaluronic acid, and alginic acid, or biodegradable polyesters, polyanhydrides, poly (ortho esters), polyphosphazenes, or polysaccharides (see, Park et al., *Molecules* 10 (2005) 141-161).

Compositions in which one chemical is microencapsulated as indicated above are well-known for delivery of pharmaceutical agents. See Shalaby and Jamiolkowski, U.S. Pat. No. 4,130,639; Buchholz and Meduski, U.S. Pat. No. 6,491,748. However, in virtually all of such compositions, it is the therapeutic agent itself that is microencapsulated, and the therapeutic agent is not produced by a reaction of microencapsulated reagents. Nitric oxide releasing polymers have been described for medical articles that involve NO adducts/donors. See e.g. Arnold, U.S. Pat. No. 7,829,553 (carbon-based diazeniumdiolates attached to hydrophobic polymers); Knapp U.S. Pat. No. 7,135,189 (a nitrosothiol precursor and a nitric oxide donor).

Applications of embodiments of the present invention include direct application of the microencapsulated reactants to wounds, dressings for wounds, surgical dressings, bed-pads for patients who have (or might develop) bedsores, socks and other garments for diabetics and other patients with circulatory impairment, and orthopedic casts, as well as for local delivery of NO for use as a vasodilator in the treatment of sexual dysfunction. The invention also meets a need in which one desires to have a small but long-lasting dose of NO associated with medical articles routinely implanted or inserted into the body such as vascular and other stents, catheters, pacemakers, defibrillators, heart assist devices, artificial valves, electrodes, and orthopedic screws and pins.

The invention can be packaged in a wound dressing or bandage so that a part of the dressing holds a mixture of particles that contain one microencapsulated reagent with other particles that contain another microencapsulated reagent. This part of the dressing also incorporates a material having water retention properties that enable maintenance of the appropriate amount of moisture to maintain the particles in a wet environment. Wetting the dressing initiates the reaction of the reagents, and the dressing begins to release NO. The dressing is structured so that the NO is released near the wound.

One embodiment of the present invention provides for extended release of NO from a layered pad that has multiple applications. It is shown in cross-section in FIG. 1A. A mixture of two or more types of microparticles 1 is contained between two layers 2 and 3, at least one of which is a bodyside-facing layer that will transmit gaseous NO, and at least one of which is an outward-facing impermeable layer or has moisture-retention properties that permit transmission of applied liquids to the microparticles inside and/or maintenance of the microparticles in a moist environment. In applications where it is desirable to retain NO on one side of the pad, one of the layers 2 or 3 is impermeable to NO. In the mixture of two or more types of sub-millimeter-scale microparticles, each type of particle comprises only one kind of microencapsulated reactant. The combination of reactants evolved from the particles in an aqueous environment produces NO. When water is introduced to the pad, the reactants begin to be released, and NO production begins.

In certain embodiments, the outer layers may be separated by a spacer layer 4 shown in FIG. 1B, which serves to maintain the spacing between the outer layers and also keeps the layer of microparticles in place. The reagent-containing microparticles may be embedded in or otherwise affixed to the spacer layer 4 or to an inner surface of either of the outer layers 2 or 3.

Pads of the type shown schematically in FIG. 1 can be prepared to any prescribed size and shape. The vertical dimensions of FIGS. 1A-C are not to scale, and the water absorbing material 5 may be much thicker than the reagent-containing pad.

Such pads have multiple applications. They can be applied to a wound simply by placing the pad on the wound and affixing it by a covering of a suitable layer of adhesive surgical tape. They may be incorporated in a pre-manufactured bandage or dressing. Alternatively, the bandage or dressing may be configured with a pouch that contains microencapsulated reagents that react to produce NO. The reagents additionally can be affixed to different layers of material, which are then assembled together to form the completed bandage or dressing.

Other configurations of the pad shown in FIG. 1 can serve as a long-lasting antimicrobial wipe cloth. The pads may be adapted and dimensioned as inserts for garments such as socks or leggings for patients with circulatory impairment. With an appropriate treatment of the edges of the material, and structure of the pad to contain the microparticles, the pad itself can also serve as the fabric for socks, gloves and other garments for patients with circulatory impairment. These garments may be activated by the moisture naturally available from the patients' skins or water may be added for activation.

Another embodiment of this invention is a bed-pad shown in FIG. 1C that comprises the microparticle-containing pad described above with an absorbent or permeable layer 5 and an impermeable layer 6 situated beneath it. This absorbent bed-pad is appropriate for patients who have or are beginning to develop decubitus ulcers (bedsores). Such patients produce modest amounts of moisture through incontinence and perspiration. The moisture will activate the NO producing pad, and excess moisture will be absorbed by the layer beneath the pad. This arrangement will have the effect of bathing the bedsore in NO which will stimulate healing and prevent further enlargement of the ulcerated area.

In a different application, small doses of NO, topically applied to the penis, have been shown to be very effective in rapid stimulation of penile erection in male rats (Han et al., *Journal of Sexual Medicine* 7 (2010) 224). The present invention provides such a topical application of NO for similar effect in humans. Present systemic drugs for sexual dysfunction have multiple negative side effects and take some time before becoming effective. A fast-acting, topical treatment is highly desirable in terms of its controllability and anticipated lack of systemic side effects. The NO generating reactants may be provided as a dry coating on dressings that are adapted for placement on erectile tissue. One example would be the interior of dressings such as male or female condoms. Wetting of the dressing for application to the erectile tissue activates the reactants that then release NO over an extended period of time.

Another embodiment of this invention is a condom having the inner surface coated with a coating comprising a mixture of individually-microencapsulated reagents which, when in aqueous solution, react together to produce NO. The microparticle size range for this embodiment is between 0.01 and 100 microns with the range of 1 to 10 microns being preferred. The smaller particles facilitate their preparation in a coating that is adherent to the inner surface of the condom and also provide a NO release on a time scale of minutes instead of hours. In employing one such embodiment, the user would apply an aqueous compound such as K-Y Jelly (manufactured by McNEIL-PPC, Inc., Ft. Washington, Pa.) to the erectile tissue prior to putting on the condom. As the microparticles come into contact with the aqueous compound, NO release begins. The NO released is contained by the condom until it is absorbed transdermally into the erectile tissue, stimulating and prolonging its erection.

Another embodiment of this invention is a sexual arousal gel kit comprising a container of an aqueous gel compound similar to K-Y Jelly and a moisture-proof package of a mixture of individually-microencapsulated reagents which, when in aqueous solution, react together to produce NO. The package is opened and mixed with the aqueous gel prior to use, and applied to the external genitalia of male and/or female users to stimulate blood flow therein, thereby promoting penile and clitoral erections. Such a kit is useful for treatment of sexual dysfunction and for enhancing sexual satisfaction in males and females.

While clinical studies with humans have not been performed, studies with rats have suggested that the NO gel composition described by Seitz et al. (U.S. Pat. No. 6,103,275) stimulates hair growth. It is known that topical vasodilators such as Minoxidil can be effective in mitigating hair loss and stimulating hair growth in humans, and it is likely that topical application of long-lasting low dose NO, which is a potent vasodilator, will have a therapeutic effect for hair loss. Thus another application of the extended release formulations disclosed herein lies in devices and compositions that mitigate hair loss and stimulate hair regrowth. One particular embodiment is a skull-cap comprising the material shown in FIG. 1 for use in treatment of hair loss. The cap is made to fit over the balding areas of the patient's head, is applied and moistened with water to activate it.

Example 1

Demonstration of Time-Release of Reagent from One Type of Particle

Microparticles having 10% by weight sodium nitrite ($NaNO_2$) in a zein matrix were prepared by spray drying a solution of sodium nitrite, zein and a volatile solvent. Zein is a proline-rich protein obtainable from corn that can be used in processed foods and pharmaceuticals as a coating and encapsulation matrix agent. It is classified as generally recognized as safe (GRAS) by the U.S. Food and Drug Administration. The solution was 10% zein (Flo Chemicals, 29 Puffer St., Ashburnham, Mass. 01430 (Lot F40000111C6)) dispersed in a mixture of 90:10 ethanol: water. The solution was dispersed into the dryer using a spinning disk atomizer. The microparticles formed in this way had diameters ranged between 10 and 100 microns and included a matrix of zein throughout which sodium nitrite is distributed. The zein is not water soluble, and when the microparticles are exposed to water, the water slowly diffuses into the zein matrix, dissolves the $NaNO_2$, and a solution containing $NaNO_2$ slowly diffuses back out of the particle, thereby producing a release of the $NaNO_2$ over a substantial period of time.

Figure 2:
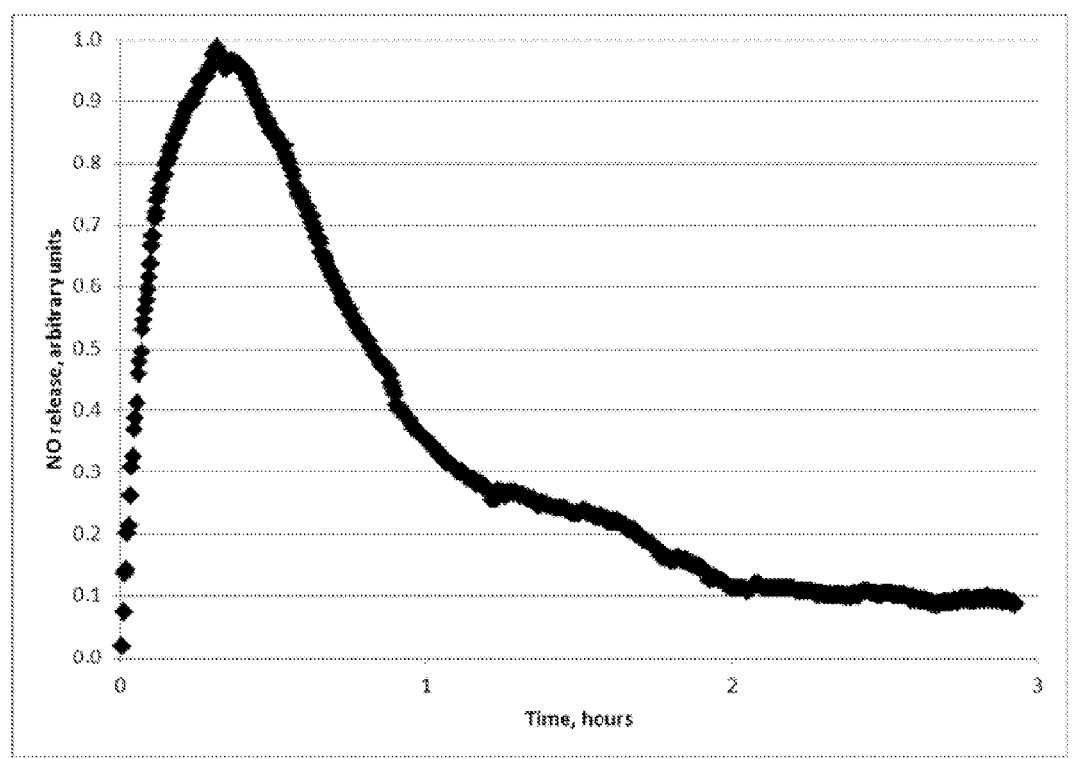
FIG. 2 shows the NO release when 10 mg of particles comprising $NaNO_2$ microencapsulated with zein (a plant protein) are introduced to an acid solution of ascorbic acid as described in EXAMPLE 1.

One hundred milliliters (100 ml) of water solution containing 5.6 g citric acid, 5.2 g of ascorbic acid and 0.3 g of PE9010 (a preservative manufactured by Schülke and Mayr, 30 Two Bridges Road Suite 225, Fairfield, N.J. 07004, USA) was prepared. Forty milliliters (40 ml) of this solution was placed in a beaker. The NO concentration in the solution was monitored with an inNO-T nitric oxide measuring system with an amiNO-700 probe (Innovative Instruments, Inc., Tampa, Fla. 33637). Ten milligrams (10 mg) of microparticles comprising sodium nitrite microencapsulated with zein were added to the solution at the time designated zero (0) and the NO content of the solution was recorded after to their addition, with the result being shown in FIG. 2. The curve of FIG. 2 shows that the NO production initiated when the microparticles were added, rose quickly to a peak and then diminished significantly during a 3-hour period. NO that is produced evolves from the liquid on a time scale of about 20 minutes, so the measured NO profiles are characteristic of the production rate of NO from the reaction of sodium nitrite emanating from the microencapsulated particles with the acids in the liquid according to reactions (1)-(3) above.

Example 2

Demonstration of Minimal NO Production when Microencapsulated Reagents are Exposed to an Excess of Water Microparticles having 10% ascorbic acid in a zein matrix were prepared by spray drying a solution of ascorbic acid, zein and a volatile solvent. The microparticle diameters ranged between 10 and 100 microns. Ten milligrams (10 mg) of these microparticles were mixed with 10 mg of microparticles of the type used in EXAMPLE 1. The mixture was added to a beaker containing 40 ml deionized water, which was continuously stirred. The NO content of the water was monitored with the same apparatus used in EXAMPLE 1. During three hours of monitoring, no detectable NO was observed.

Example 3

Demonstration of Long-Lived NO Production when Microencapsulated Reagents are Incipiently Wet Microparticles having 10% by weight sodium nitrite in an ethyl cellulose matrix were prepared by spray drying a solution of sodium nitrite, ethyl cellulose and a volatile solvent. The solution was 12.5% ethyl cellulose (Ethocel Standard 7 from Dow Chemicals (Lot U105013T01)) dispersed in ethanol. The solution was dispersed into the dryer using a spinning disk atomizer. The microparticle diameters ranged between 10 and 100 microns. Additionally, microparticles having 10% by weight ascorbic acid in an ethyl cellulose matrix were prepared by spray drying a solution of ascorbic acid, ethyl cellulose and a volatile solvent. The solution was 12.5% ethyl cellulose (Ethocel Standard 7 from Dow Chemicals (Lot U105013T01)) dispersed in ethanol. The solution was dispersed into the dryer using a spinning disk atomizer. These microparticle diameters also ranged between 10 and 100 microns.

Figure 3:
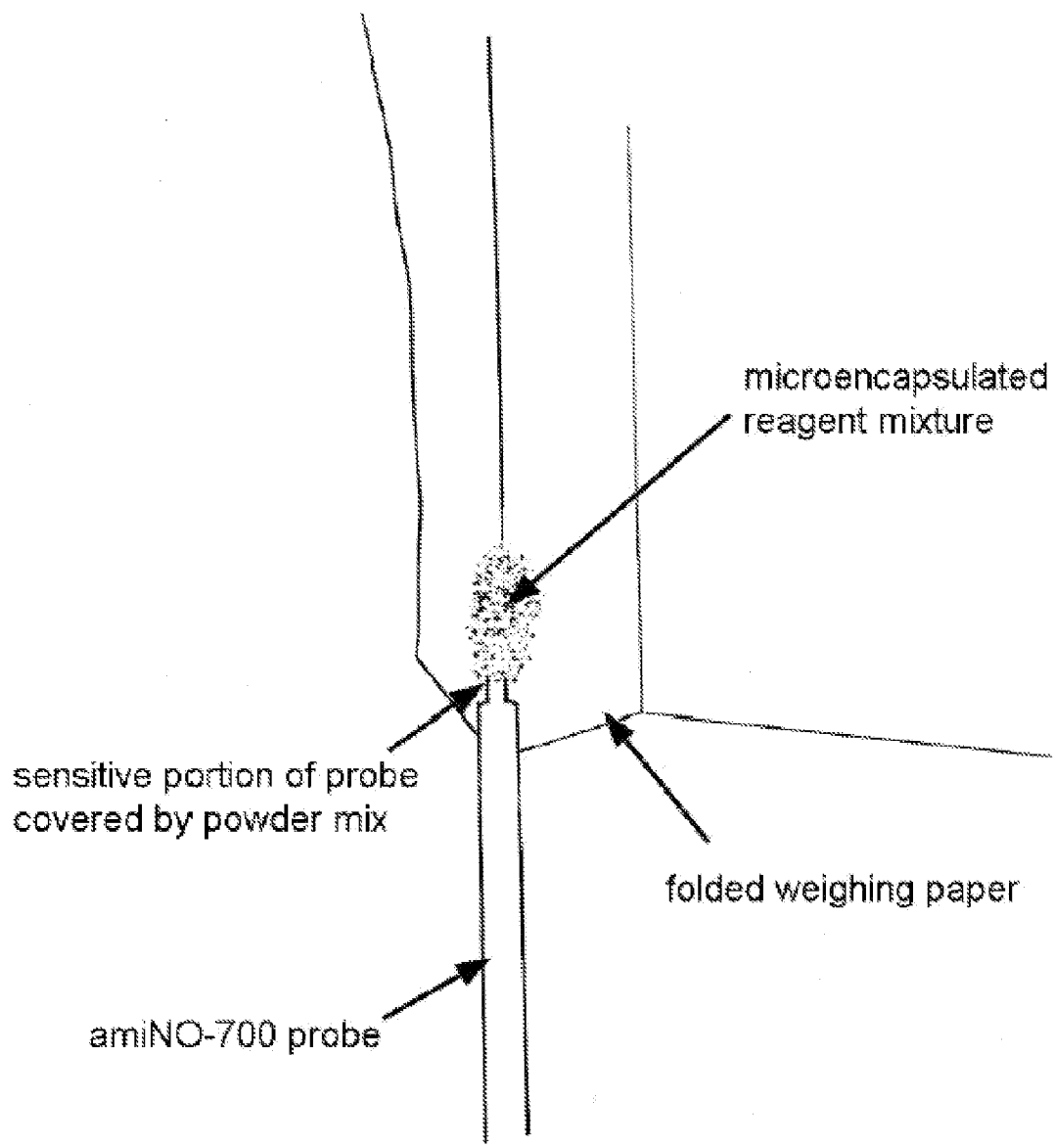
FIG. 3 shows the arrangement of amiNO-700 probe and microencapsulated powder mix used in EXAMPLE 3.
Figure 4:
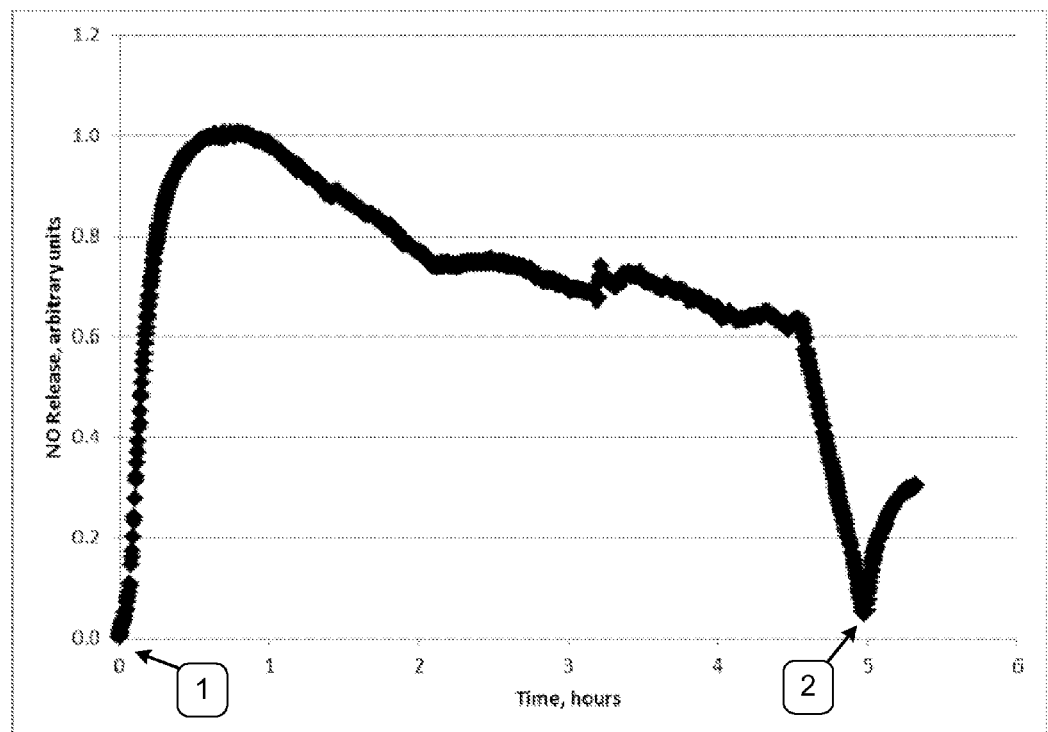
FIG. 4 shows the NO release when 10 mg of particles comprising ascorbic acid microencapsulated in an ethyl cellulose matrix and 10 mg of particles comprising $NaNO_2$ microencapsulated in an ethyl cellulose matrix are incipiently wet as discussed in EXAMPLE 3.

Ten mg of each type of particle was mixed together and placed on piece of weighing paper that contained the powder in a small fold in the paper. The amino-700 probe tip was inserted into and completely covered by the powder mix as shown in FIG. 3. Two hundred microliters (200 µl) of deionized water was used to wet the powder mixture (at the time labeled "1" on FIG. 4), and the excess water was absorbed by the paper. Thus the particles remained in a state of incipient wetness where water resided primarily on their surfaces and in narrow interstices between the particles. The NO signal was recorded for the next five and one-half hours. That recording in FIG. 4 shows that NO production rose during the first half hour, and then decreased very slowly for the next four hours. Abruptly, after a total time of four and one-half hours, the NO signal dropped linearly toward zero. The drop in signal is concluded to be due to complete evaporation of the water in the sample. An additional one hundred microliters (100 µl) was added after the signal dropped (at the time labeled "2" in FIG. 4, and the signal again increased, confirming this conclusion. This result is surprising because of the longevity of the NO release compared to that observed in EXAMPLE 1.

Example 4

Demonstration of Long-Lived NO Production with Microencapsulated Reagents in a Moist Paste Ten milligrams (10 mg) each of the particles used in EXAMPLES 1 and 2 (i.e. particles comprising 10% by weight sodium nitrite encapsulated in a zein matrix and particles comprising 10% by weight ascorbic acid in a zein matrix) were mixed together and placed in a small plastic half-cylinder. The amino-700 probe tip was completely covered by the particle mix in an arrangement similar to that used in EXAMPLE 3 and shown in FIG. 3. A volume of 200 µl of deionized water was used to wet the mixture to a consistency of a moist paste, and the NO signal was recorded for the next eight hours.

Figure 5:
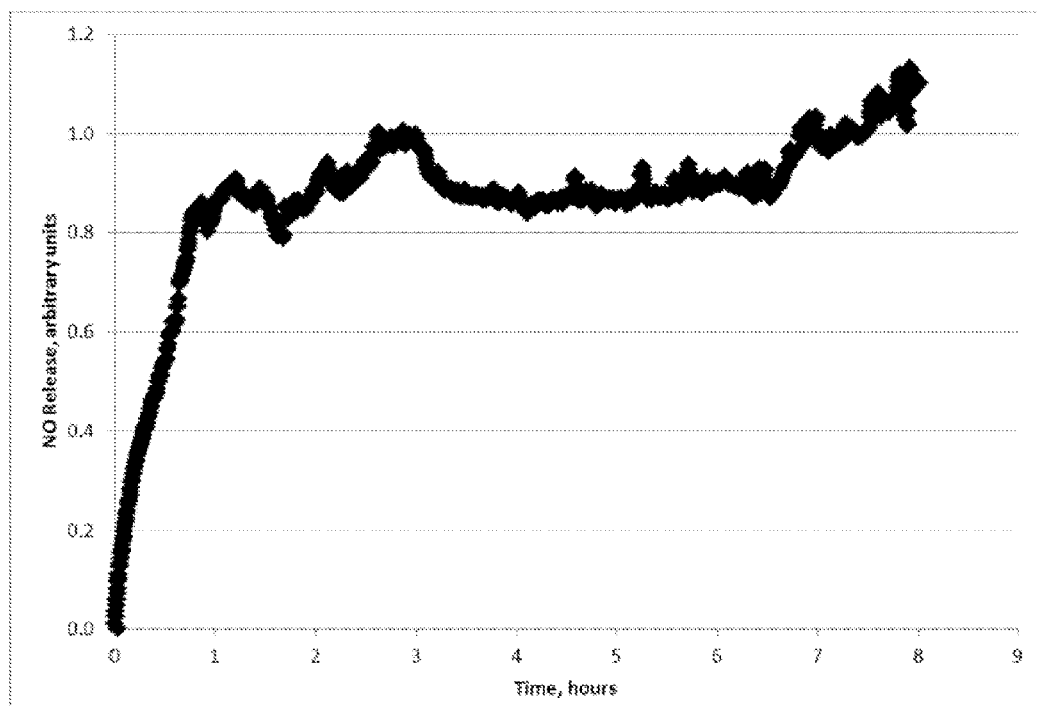
FIG. 5 shows the NO release when 10 mg of particles comprising ascorbic acid microencapsulated in a zein matrix and 10 mg of particles comprising $NaNO_2$ microencapsulated in a zein matrix are formed into a wet paste with 200 microliters of water as discussed in EXAMPLE 4. The paste is formed by adding water to the mixture of particles at the time designated zero (0).

That recording is shown in FIG. 5. NO production rose slowly for the first hour, and then remained relatively constant for at least the remaining seven hours, at which time the experiment was discontinued. This result is surprising in terms of the constancy and longevity of the NO release in comparison to the result of EXAMPLE 1.

First, it was noted there is a significant difference between the amount of NO measured in EXAMPLE 2 (where there was not an observable amount of NO released) and EXAMPLES 3 and 4 (substantial NO release), even though the same weights of reagent were used in both experiments. This difference is surprising, but without being limited by theory, one may consider several possibilities as to why this is the case. The environment for the NO production process in EXAMPLE 2 is substantially different from that in EXAMPLES 3 and 4, and these differences highlight some of the aspects of the present invention.

NO is unstable in the air and in vivo and its use as a therapeutic agent requires that it be produced by reaction of chemical precursors which are individually stable. In EXAMPLES 3 and 4, the reservoirs of the chemical precursors (e.g. the particles in which the reagents are microencapsulated) are maintained in close physical proximity to one another in a limited volume, and a limited amount of solvent residing within that same volume is used to extract and process the reagents to form NO. To promote a long-duration time release, these chemical precursors are also microencapsulated as described above. EXAMPLE 2 is characteristic of what would happen if one sought to produce a time-released dose of NO simply by introduction of two microencapsulated reagents into a water-based pharmaceutical preparation having a significant volume or simply introduced them into the bloodstream or the alimentary tract. The reagents that evolve from the encapsulation vehicles are quickly diluted, and their rate of reaction with each other will be slowed very significantly. Additionally, in the particular case of production of NO through reactions (1)-(3), it is also known that the reaction rate is pH sensitive, and decreases to zero as the pH approaches a neutral pH of 7. In EXAMPLE 2, the only agent that lowers the pH of the solution is the ascorbic acid evolving from the microencapsulation vehicle particles. When the ascorbic acid is very dilute, it cannot bring the pH of the entire solution to a value that is low enough to allow the reaction producing NO to proceed at any significant rate. However, in the cases of EXAMPLES 3 and 4 (which are embodiments of the present invention), the reagents are being dispensed from particles that are in close proximity to one another, and the amount of solvent into which the reagents are dispensed is very small. Therefore the local reagent concentrations are orders of magnitude higher than those appropriate to EXAMPLE 2. The reaction to produce NO can proceed more rapidly, both because of the high reagent concentrations, and because the much higher local concentration of ascorbic acid substantially decreases the pH so that the reaction can proceed at a greater rate, producing more NO per unit time.

A further surprising result is the marked contrast between the time dependence of NO production in EXAMPLE 1 (wherein the NO production diminishes very substantially within three hours) and that observed in EXAMPLE 3 (where the NO production continues for about five hours) and EXAMPLE 4 (where the NO production continues at a relatively constant level for at least 8 hours).

In EXAMPLE 1, particles containing microencapsulated $NaNO_2$ are introduced to an acid solution comprising citric and ascorbic acids. Immediately upon introduction of these particles, the solution begins to diffuse into the particles and to dissolve the encapsulated $NaNO_2$. Subsequently, the reactions (1)-(3) producing NO take place either within the particle itself, or after dissolved $NaNO_2$ diffuses out of the particle into the acid solution. This scenario is characteristic of the usual application of microencapsulated time-release compositions wherein an active component is microencapsulated and is subsequently introduced into an environment in which that active component is released from the microencapsulation vehicle, and the active component becomes a minor constituent of that environment. Generally, the release rate of the microencapsulated substance decreases with time as the supply of microencapsulation material diminishes within the microencapsulation vehicle. This characteristic decrease is seen in FIG. 2, which shows the time-dependence of NO production in EXAMPLE 1.

While the NO production in EXAMPLE 1 decreases substantially over a three hour period, the NO production in EXAMPLES 3 and 4 persists at a fairly constant rate for at least seven hours. The difference is surprising and is particularly useful in some applications such as dressings for wounds, because one desires to keep the wound bathed in a low concentration of NO to promote healing and provide protection against bacteria. Without being limited by theory, it is believed that the explanation for this useful modification of the time-release characteristic again lies in the placement of the reservoirs of the chemical precursors (e.g. the particles in which the reagents are microencapsulated) together in close physical proximity to one another within a limited volume, and use of a limited amount of solvent residing within that same volume to extract and process the reagents to form NO. In this configuration, the kinetics of the process of extraction and reaction of the microencapsulated reagents is likely to be more complex than it is in the case of EXAMPLE 1, which represents the traditional application of delayed time release of a microencapsulated agent. In EXAMPLES 3 and 4, where the extraction of microencapsulated reagents from the sub-millimeter-scale particles takes place with a miniscule amount of water, the concentrations of the reagents at the surface of the particles is much higher. It is possible that these local elevated concentrations modify the dynamics of diffusion of the reagents out of the particles, slowing the diffusion because the reagent concentration gradient between the inside and outside of the particle is smaller.

Additionally, with the high concentrations of reagents present, it becomes more likely that one dissolved reagent will diffuse into a particle containing another reagent with which it reacts. To the extent that this occurs, gaseous NO may be produced within the particle. The production of a gas within the channels where diffusion is taking place is likely to slow the diffusion of liquids in those same channels which is the essential to bring the reagents out of the particles within which they are microencapsulated. Thus the total NO production rate may be diminished because a small amount of NO being formed inside the particles.

Example 5

Demonstration of Long Time-Release of NO from a Microencapsulated Reagent in the Presence of Different Concentrations of Gelling Agent A first lower viscosity gel-form acid solution was prepared as follows: 0.73 grams of hydroxyethyl cellulose (HEC), 5.6 g citric acid, 5.2 g of ascorbic acid, and 0.3 g of PE9010 was mixed with water to make up 100 ml. A second higher viscosity gel form acid solution was prepared as follows: 2.18 grams of hydroxyethyl cellulose (HEC), 5.6 g citric acid, 5.2 g of ascorbic acid, and 0.3 g of PE9010 was mixed with water to make up 100 ml. The only difference between these solutions and that used in EXAMPLE 1 was the presence of the gelling agent, HEC, which is a water-soluble polymer derived from cellulose. The HEC used in this example had a mean molecular weight of 750,000, and when the HEC is mixed in, the solution becomes a high-viscosity gel. Both the solutions prepared with HEC have an increased viscosity compared to the solution used in EXAMPLE 1. Both the gel solutions are easily stirred with laboratory stirring apparatus, but the higher-concentration-HEC solution is considerably more viscous.

Twenty-five milliliters (25 ml) of the first solution prepared was placed in a beaker and continuously stirred. The NO concentration in the solution gel was monitored with an inNO-T nitric oxide measuring system with an amiNO-700 probe. Ten milligrams (10 mg) of the $NaNO_2$ microparticles of the type used in EXAMPLE 1 were introduced to the gel solution and the NO concentration in the gel solution was recorded for three hours. When the microparticles were introduced to the gel solution, production of small bubbles around the microparticles was observed.

Twenty-five milliliters (25 ml) of the second solution prepared was placed in a beaker and continuously stirred. The NO concentration in the solution gel was monitored with an inNO-T nitric oxide measuring system with an amiNO-700 probe. Ten milligrams (10 mg) of the $NaNO_2$ microparticles of the type used in EXAMPLE 1 were introduced to the gel solution and the NO concentration in the gel solution was recorded for eight hours. When the microparticles were introduced to the gel solution, bubble production was observed to be much less pronounced and to take place over a shorter period of time than was observed when introducing the microparticles to the first solution.

Figure 6:
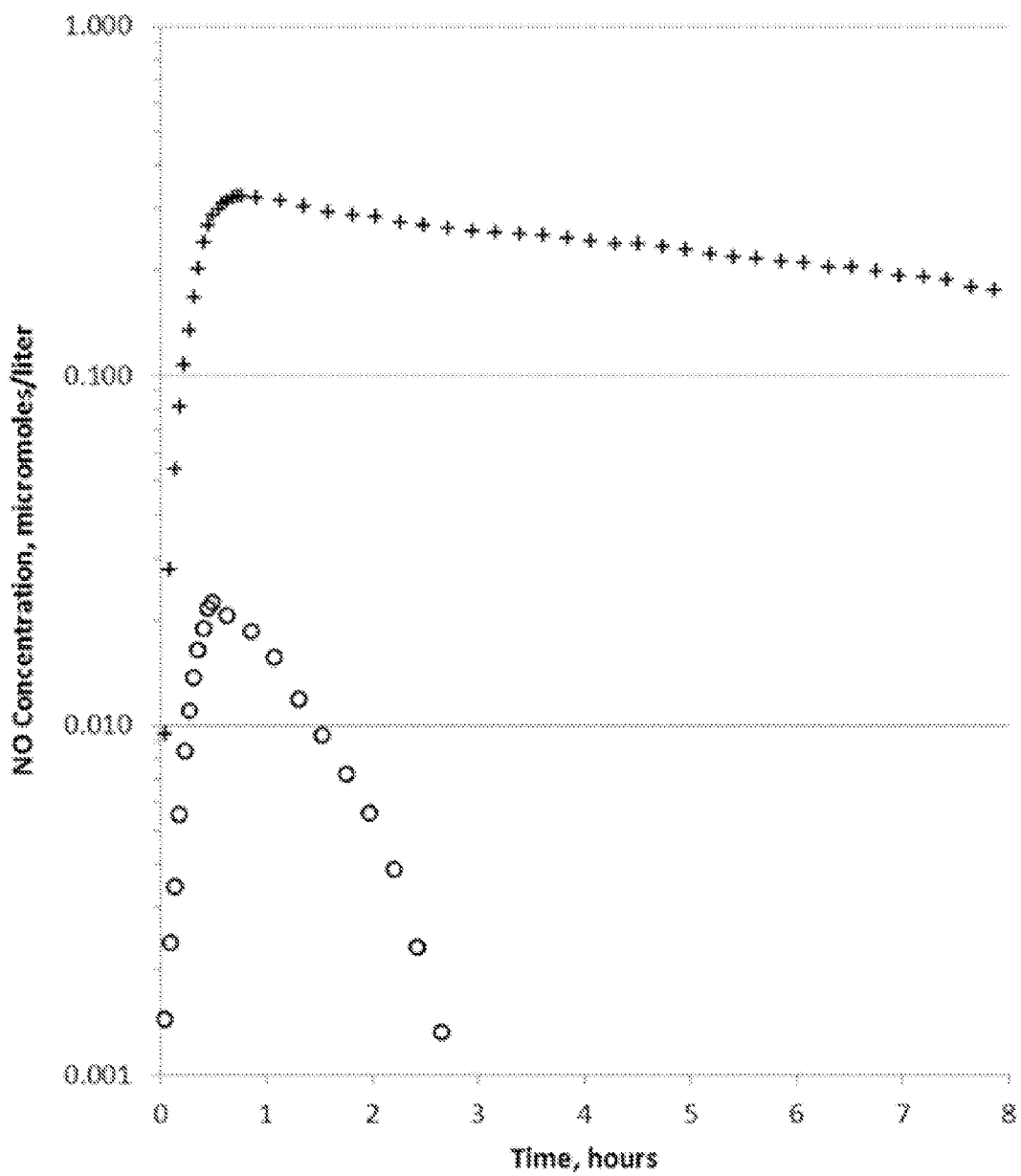
FIG. 6 shows data from EXAMPLE 5, which are the measured NO concentrations in the first lower-HEC-concentration (circles) and second higher-HEC-concentration (crosses) solutions, subsequent to the introduction of ten milligrams (10 mg) of $NaNO_2$ microparticles of the type used in EXAMPLE 1. The HEC concentrations in the first and second solutions are 0.73 g/100 ml and 2.18 g/100 ml, respectively. The peak measured NO concentrations in the first and second solutions are 0.022 micromoles/liter and 0.324 micromoles/liter, respectively. For both curves shown, the microencapsulated sodium nitrite is introduced at the time designated zero (0).

FIG. 6 shows a comparison of the measured NO concentrations in the first lower-viscosity (circles) and second higher-viscosity (crosses) solutions, subsequent to the introduction of ten milligrams (10 mg) of $NaNO_2$ microparticles of the type used in EXAMPLE 1. The lifetime of the NO release in the solution with the higher concentration of HEC is markedly longer. The NO concentration in the second solution (containing 2.18 g/100 ml HEC) reaches a peak that is more than an order of magnitude higher than that reached in the first solution and decays to half its peak value in about eight hours, while the NO concentration in the first solution (containing only 0.73 g/100 ml HEC) decayed to half its peak value in about one hour. The difference is dramatic. The NO released in the reaction of the initially-microencapsulated reagent is transferred much more effectively to the solution when HEC is present at the higher concentration. Both the long duration and high concentration of the NO release to the gel solution with a high HEC concentration are surprising and useful in therapeutic applications where a long-duration, therapeutically-effective dose of NO is desired.

Without being bound by theory there are two effects to consider in understanding the difference between the evolution of the NO concentration in the solutions with the high and low concentrations of the gelling agent, HEC. These effects are the kinetics of the removal of the $NaNO_2$ from the microparticles and the transfer of NO formed into the liquid.

The kinetics of the removal of $NaNO_2$ from the microparticles depends on both the diffusion of water into the particles and the diffusion of solution containing dissolved $NaNO_2$ back out of the particles. The diffusive flow of solution within the particle takes place in irregularities in the particle that provide channels for the solution flow. HEC is a large, water-soluble polymer molecule, and when it is present in the solution, it substantially increases the viscosity of the solution and inhibits diffusive flow of the solution within the channels in the microparticle. Therefore the release of $NaNO_2$ to the solution outside the particle is substantially slowed. This slowing of the diffusion in and out of the microparticle is anticipated to be proportional to the HEC concentration; and such a slowing of diffusion is consistent with the reduction observed in the amount of bubbles formed around the particles when they are introduced to the high-HEC-concentration solution.

When the $NaNO_2$-rich solution finally does diffuse out of the microparticle, the $NaNO_2$ reacts rapidly in the acid environment there to produce NO. NO dissolves fairly slowly into the ambient liquid, and if the NO production rate is relatively high, NO-filled bubbles will form on the surface of the microparticles, and when they become large enough, they will migrate into the liquid. Once the bubble becomes free-floating in the liquid, it will travel to the surface of the liquid, pop, and disperse the NO into the air above the liquid. During the process of bubble formation and transport through the liquid, the NO is also dissolving into the liquid. If the bubble formation process is rapid, the bubbles reside on the surfaces of the microparticles for a short time, they are rapidly released into the liquid. If the bubbles rise through the liquid rapidly, they effectively transport a substantial fraction of the NO out of the liquid, and it is never dissolved.

HEC, in proportion to its concentration, slows the diffusion of $NaNO_2$ out of the microparticles and therefore slows the rate of bubble formation, which initially takes place on the microparticle surfaces. In turn, this slower bubble formation provides for an extended period of contact between gaseous NO in the bubbles and the liquid, increasing the fraction of NO that dissolves into the liquid. In fact, if the release of NO from the microparticle is slow enough, the release rate of NO may become equal to or smaller than the rate of NO dissolution in the liquid, no free bubbles will be released into the liquid, and all the NO will be dissolved. Thus, since the higher HEC concentration reduces the production rate of NO, a larger fraction of the NO will be dissolved in the higher-HEC-concentration solution.

Another factor that increases the amount of NO dissolved in the higher-HEC-concentration solution is that if the NO bubbles leave the surfaces of the microparticles and become free bubbles of NO, they reside in the liquid for much longer times because the higher-HEC concentration solution is a considerably more viscous gel than the lower-HEC concentration solution. This slow transport of free NO bubbles provides an additional opportunity for additional NO to become dissolved in the liquid.

The kinetic effects described above are more pronounced at higher concentrations of HEC. Therefore, in the higher-concentration HEC solution, both because of the reduced rate of NO formation, and the consequent improvements in transfer of NO to the liquid, the higher-HEC-concentration solution develops a very significantly higher concentration of NO, and maintains a high concentration of NO for a substantial period of time, as shown in FIG. 6.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An extended release generator of therapeutic nitric oxide that includes at least two separate reactant components that are not mixed and do not generate or include nitric oxide (NO) until the extended release generator of therapeutic nitric oxide is applied to a patient, the extended release generator comprising:
- a first reactant component including a nitrite salt in a chemically-stable form provided by microencapsulation in a polymer matrix that forms a dry environment but that is diffusible to acidic aqueous solutions; and
- a second reactant component including a viscous aqueous acidified gel composition comprising an acidifying agent, a reductant, and a gelling agent, characterized by having a viscosity of that provided by aqueous solutions of from 0.73 to 2.18 grams per 100 mL of an aqueous solution of hydroxy ethyl cellulose (HEC) having a mean molecular weight of 750,000, wherein the acidifying agent and reductant may be the same agent,
- and wherein the second reactant component has sufficient acidity and reductive capability to covert the nitrite salt to nitric oxide and slow the oxidation of nitric oxide to nitrogen dioxide.

2. The extended release generator of therapeutic nitric oxide of claim 1, wherein the nitrite salt is selected from one or more of the group consisting of: sodium nitrite, potassium nitrite, calcium nitrite, alkali metal nitrite and alkaline earth nitrite.

3. The extended release generator of therapeutic nitric oxide of claim 1, wherein the acidifying agent is selected from the group consisting of: citric acid, lactic acid, boric acid, glyceric acid, formic acid ascorbic acid and combinations thereof.

4. The extended release generator of therapeutic nitric oxide of claim 1, wherein the acidifying agent is boric acid.

5. The extended release generator of therapeutic nitric oxide of claim 1, wherein the reductant is selected from the group consisting of: ascorbic acid, an ascorbic acid derivative, ascorbate salts, tocopherols, erythrobates, carotenoids, tocotrienols, thiols, and combinations thereof.

6. The extended release generator of therapeutic nitric oxide of claim 1, wherein citric acid is the acidifying agent and ascorbic acid or ascorbic acid derivative is the reductant.

7. The extended release generator of therapeutic nitric oxide of claim 1, wherein the ascorbic acid or ascorbic acid derivative is the acidifying agent and the reductant.

8. The extended release generator of therapeutic nitric oxide of claim 1, wherein the gelling agent is selected from the group consisting of: hydroxymethyl cellulose, hydroxyethyl cellulose, gelatin, agar, natural gums, starches pectins, and combinations thereof.

9. The extended release generator of therapeutic nitric oxide of claim 1, wherein the polymer matrix of the first reactant component comprises a polymer selected from the group consisting of: ethyl cellulose, natural polymers, hyaluronic acid, alginic acid, biodegradable polyesters, polyanhydrides, poly(ortho esters), polyphosphazenes, polysaccharides and combinations thereof.

10. The extended release generator of therapeutic nitric oxide of claim 9, wherein the natural polymer is zein.

11. A kit for providing extended release therapeutic nitric oxide to a patient comprising at least two separated reactant components that do not generate or include a nitric oxide (NO) until the reactant components are mixed at a time that they are applied to a patient, the reactant components including:
- a first reactant component including a nitrite salt provided in a chemically stable form as a dry microencapsulated reactant that is diffusible to acidic aqueous solutions; and
- a second reactant component including an activating volume of a viscous aqueous acidified gel composition comprising an acidifying agent, a reductant, and a gelling agent, characterized by having a viscosity of that provided by aqueous solutions of from 0.73 to 2.18 grams per 100 mL of an aqueous solution of hydroxyethyl cellulose (HEC) having a mean molecular weight of 750,000, wherein the acidifying agent and reductant may be the same agent,
- and wherein the second reactant component has sufficient acidity and reductive capability to convert the nitrite salt to nitric oxide and slow the oxidation of nitric acid to nitrogen dioxide.

12. The kit of claim 11, wherein ascorbic acid or a derivative thereof is the acidifying agent and the reductant.

13. The kit of claim 11, further comprising an instruction to the patient to apply both the reactant component including the microencapsulated nitrite salt and the separate reactant component including the activating volume of aqueous acidified gel solution to a tissue in need thereof.

14. The kit of claim 11, wherein the acidifying agent is citric acid and the reductant is ascorbic acid or an ascorbic acid derivative.

15. The kit of claim 11, wherein the first reactant component salt is provided in a wound dressing or bandage and the second reactant component is provided in a premeasured container.

16. The kit of claim 11, wherein the first reactant component is provided as a coating in a condom and the second reactant component is provided in a premeasured container.

* * * * *